(12) United States Patent
Palomino

(10) Patent No.: US 11,485,718 B2
(45) Date of Patent: Nov. 1, 2022

(54) SYNTHESES AND USES OF MECHANISM-BASED NUTRITIONAL COLORANTS FROM VITAMIN C AND AMINO-CONTAINING COMPOUNDS

(71) Applicant: WALKER CANCER RESEARCH INSTITUTE, INC, Boynton Beach, FL (US)

(72) Inventor: Eduardo Palomino, Troy, MI (US)

(73) Assignee: WALKER CANCER RESEARCH INSTITUTE, INC, Boynton Beach, FL (US)

( * ) Notice: Subject to any disclaimer, the term of this patent is extended or adjusted under 35 U.S.C. 154(b) by 0 days.

(21) Appl. No.: 17/212,186

(22) Filed: Mar. 25, 2021

(65) Prior Publication Data

US 2022/0306597 A1    Sep. 29, 2022

(51) Int. Cl.
   *C07D 307/66*    (2006.01)
(52) U.S. Cl.
   CPC .................. *C07D 307/66* (2013.01)
(58) Field of Classification Search
   CPC .... C07D 415/00; C07D 307/66; A61K 31/51; A61K 31/341
   USPC .................. 514/276, 474; 544/327; 549/477
   See application file for complete search history.

(56) References Cited

PUBLICATIONS

Zeinalov et. al., Izvest. Akad. Nauk Azerbaidzhan. S.S.R. (1956), (No. 9), 17-30. (Year: 1956).*
Sakurai, et al., Nihon Daigaku Nojuigakubu Gijutsu Kenkyu Hokoku (1988), (45) 59-70. (Year: 1988).*
Poznyak, A. L.; Stopolyanskaya, L. V.; Zhurnal Neorganicheskoil khimii. / Zhurnal neorganicheskoi Khimii (1992), 37(3), pp. 602-607. (Year: 1992).*
STN Database, CAS registry No. 118665-35-3, submitted Jan. 27, 1989. (Year: 1989).*
Larisch et al. (J. Agric. Food Chem. 1996, 44, 1630-1634: Reactions of Dehydroascorbic Acid with Primary Aliphatic Amines Including N-Acetyllysine) ("Larisch").

* cited by examiner

*Primary Examiner* — Jeffrey H Murray
(74) *Attorney, Agent, or Firm* — Haug Partners LLP

(57) ABSTRACT

Embodiments of the present invention provide for syntheses and uses of mechanism-based nutritional colorants from vitamin C and amino-containing compounds, wherein the amino-containing compounds can be one of natural compounds or synthetic compounds, wherein the amino-containing compounds can be made through environmentally-friendly radical reactions that follow the antioxidant mechanism of action of vitamin C.

7 Claims, 7 Drawing Sheets

Figure 1 a) $(CN)_6K_3Fe^{+2}\text{-H} + H_2O_2 \longrightarrow (CN)_6K_3Fe^{+3} + H_2O + HO^\bullet$ b) $\text{Catalase-Heme-H} + H_2O_2 \longrightarrow \text{Catalase-Heme} + H_2O + HO^\bullet$ δ-Tocopherol δ-Tococatechol

SYNTHESES AND USES OF MECHANISM-BASED NUTRITIONAL COLORANTS FROM VITAMIN C AND AMINO-CONTAINING COMPOUNDS

FIELD OF DISCLOSURE

The present invention concerns syntheses and uses of mechanism-based nutritional colorants from vitamin C and amino-containing compounds.

BACKGROUND OF THE INVENTION

Useful natural colorants are scarce in the food and cosmetic industry, where synthetic dyes are predominant. Further, although many synthetic dyes are FDA-approved, there is an inherent threshold of toxicity in synthetic dyes that could manifest in some susceptible individuals.

Accordingly, there is a need for truly natural, non-toxic colorants.

SUMMARY OF INVENTION

The present invention provides for ketoimino compounds derived from vitamin C and the following formula:

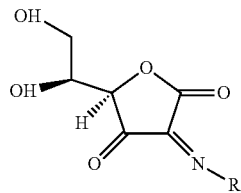

wherein R represents any amino-containing compound, natural or synthetic. According to an embodiment, the exemplary ketoimino compounds, due to their higher oxidation state and intrinsic resonance, can be highly stable and naturally endowed with a multiplicity of colors that resist changes in pH and temperature, with a solubility that can be easily modified with variations on the R substituent. According to an embodiment, when the substitutions are natural amino acids, the exemplary all-natural ketoimino compounds can mimic the colors of fruits and vegetables and, as such, can be safely used to naturally color drinks and cosmetics, and can also be used as a delivery form for vitamin C and the amino acids. In this regard, other useful compounds can be delivered through this system, including the natural vitamin B1 and amines used as drugs, such as the antidiabetic metformin. Further, the compounds described can be made through environmentally-friendly radical reactions that follow the antioxidant mechanism of action of vitamin C, described herein, in which water is used as the solvent and the byproducts are useful non-toxic materials.

BRIEF DESCRIPTION OF THE DRAWINGS

Some aspects of the disclosure are herein described, by way of example only, with reference to the accompanying drawings. With specific reference now to the drawings in detail, it is stressed that the particulars shown are by way of example and are for purposes of illustrative discussion of embodiments of the disclosure. In this regard, the description, taken with the drawings, makes apparent to those skilled in the art how aspects of the disclosure may be practiced.

FIG. 1 illustrates (a) a tripotassium hydrogen ferrocyanide reaction with hydrogen peroxide and (b) a catalase reaction with hydrogen peroxide.

DETAILED DESCRIPTION OF THE INVENTION

This description is not intended to be a detailed catalog of all the different ways in which the disclosure may be implemented, or all the features that may be added to the instant disclosure. For example, features illustrated with respect to one embodiment may be incorporated into other embodiments, and features illustrated with respect to a particular embodiment may be deleted from that embodiment. Thus, the disclosure contemplates that in some embodiments of the disclosure, any feature or combination of features set forth herein can be excluded or omitted. In addition, numerous variations and additions to the various embodiments suggested herein will be apparent to those skilled in the art in light of the instant disclosure, which do not depart from the instant disclosure. In other instances, well-known structures, interfaces, and processes have not been shown in detail in order not to unnecessarily obscure the invention. It is intended that no part of this specification be construed to affect a disavowal of any part of the full scope of the invention. Hence, the following descriptions are intended to illustrate some particular embodiments of the disclosure, and not to exhaustively specify all permutations, combinations and variations thereof.

Figure 2:
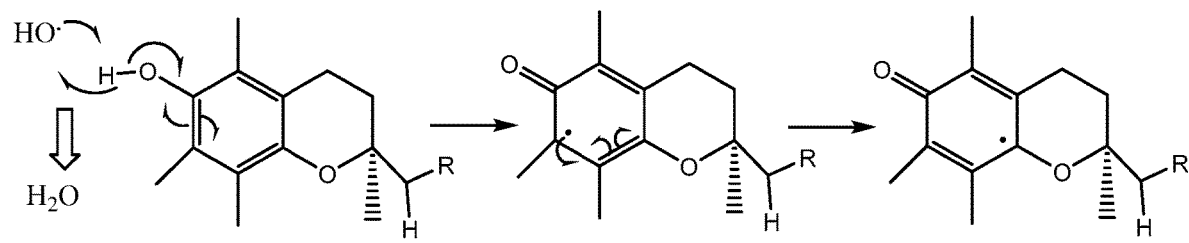
FIG. 2 illustrates a mechanism of stabilization of a radical generated by the reaction of a general vitamin E with hydroxyl radicals.

Vitamin C (ascorbic acid) is an antioxidant that sits outside the most abundant and diversified phenolic antioxidants, such as vitamin E. While the use of vitamin C and phenolic antioxidants has increased dramatically, their actual mechanisms of action have eluded researchers due, at least in part, to a lack of clean sources of an oxidant, e.g., hydroxyl radical (HO.). According to an embodiment, as depicted in FIG. 1, the hydroxyl radical can be produced by the reaction of a mono-hydrogen ferrocyanide with hydrogen peroxide ($H_2O_2$), emulating the same reaction taken place at the heme active site of the ubiquitous enzyme catalase, for which the mono-hydrogen ferrocyanide served as a chemical simile for the elucidation of the mechanism of action of the enzyme. According to an embodiment, the hydroxyl radical is very selective in its two most important reactions: hydrogen abstractions and hydroxyl additions. For hydrogen abstractions, the hydroxyl radical exclusively reacts with phenolic hydrogens. The abstraction of a hydrogen atom from the phenol stabilizes the radical HO. with the formation of water ($H_2O$) and generates a phenoxy radical stabilized temporarily by resonance as shown in FIG. 2, which eventually proceeds to a chain of events designed to stabilize permanently the radical.

Figure 3:
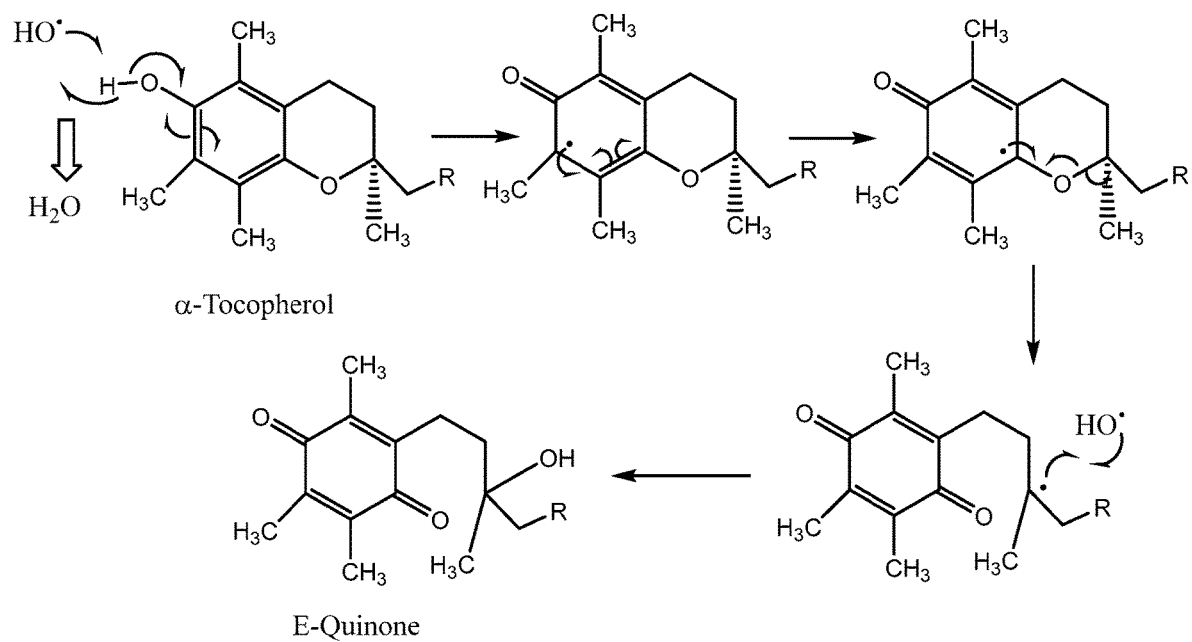
FIG. 3 illustrates a mechanism of formation of E-quinone by the reaction of α-tocopherol (one of the vitamin E structures) with a hydroxyl radical.
Figure 4:
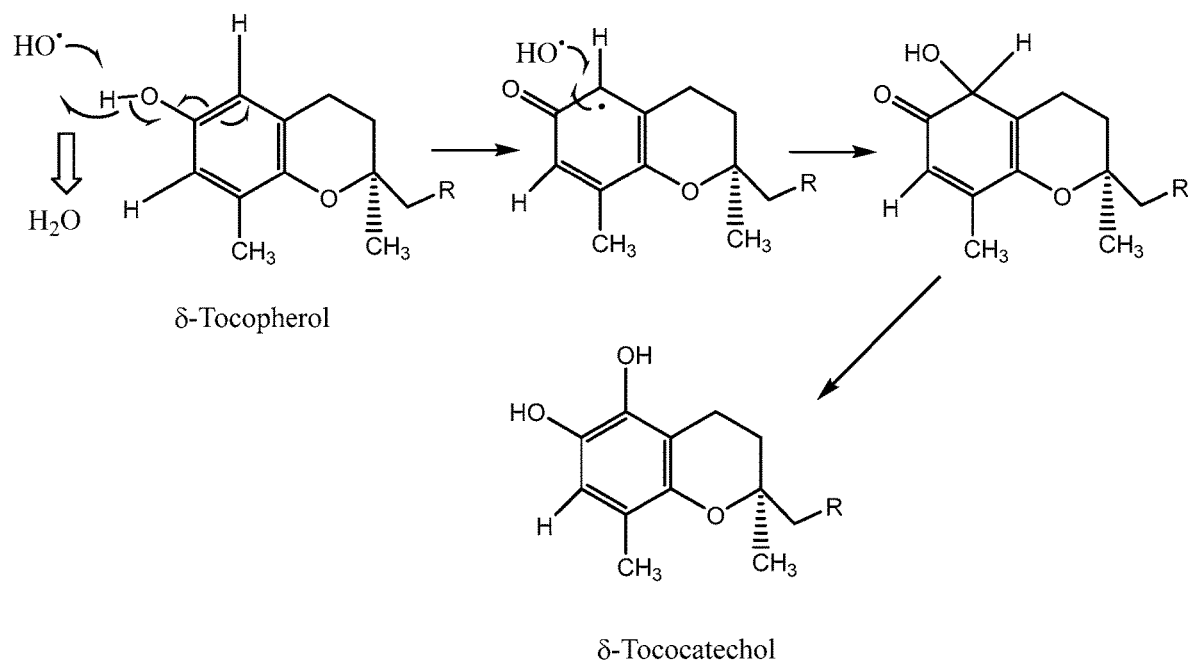
FIG. 4 illustrates a mechanism of formation of δ-tococatechol by the reaction of δ-tocopherol (one of the vitamin E structures) with a hydroxyl radical.

According to an embodiment, one effective way of stabilization is through the incorporation of another HO. radical as a hydroxyl addition producing a stable structure such as an alcohol or a phenol. The selectivity of such addition is shown in the mechanism of action of the α- and δ-tocopherols (e.g., two of the isomers of vitamin E). Although very similar in their overall structure, the δ-isomer lacks 2 methyl groups on both sides of the phenol OH compared to the methyl-saturated α-tocopherol. The phenoxy radical in either case has the two resonance positions of FIG. 2 but the full methyl-saturation of the α isomer forces the opening of the second ring through the second phenoxy oxygen producing, after hydroxylation on the side chain, the known E-quinone (e.g., see FIG. 3), a compound with structure and blood-clotting activities similar to vitamin K. The δ-tocopherol, on the other hand, can replaces an aromatic hydrogen and places a HO. radical at the least hindered site next to the original phenol, forming a catechol (S-tococatechol), without altering the original two-ring structure, as shown in FIG. 4.

Figure 5:
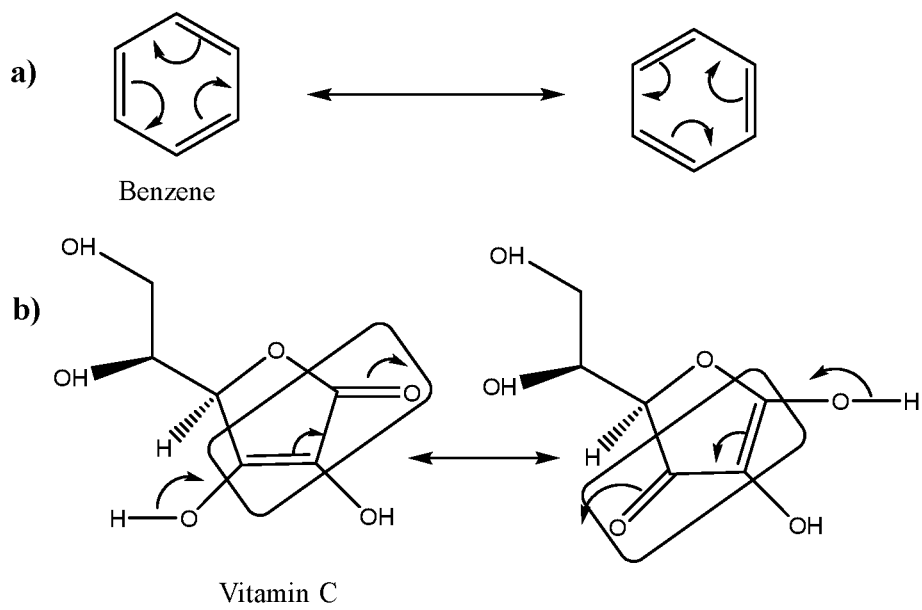
FIG. 5 illustrates the aromatic character of (a) benzene as compared to (b) Vitamin C.
Figure 6:
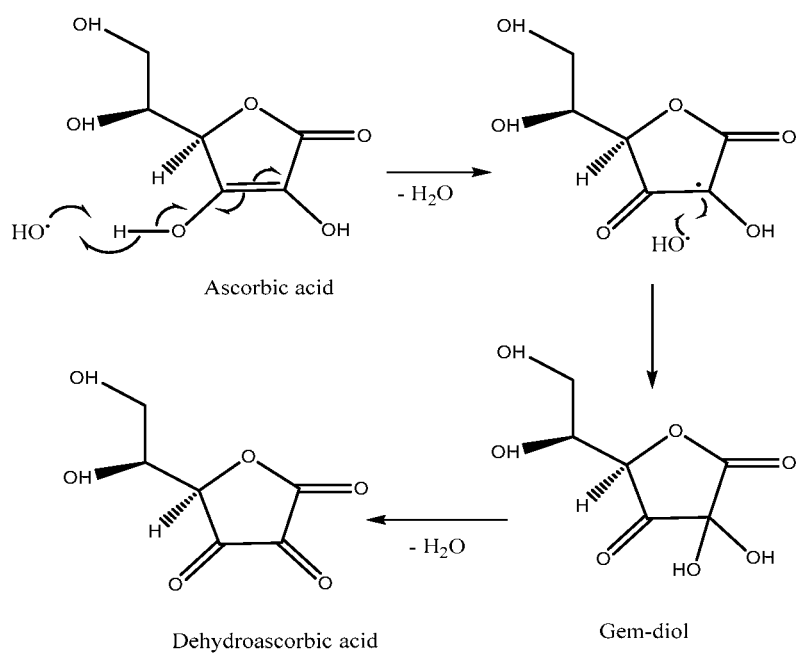
FIG. 6 illustrates a mechanism of reaction of vitamin C with hydroxyl radicals.

On the other side of the antioxidant group sits vitamin C. Although it has always been considered an aliphatic compound, its reactivity towards the hydroxyl radical makes it look like a phenol (an aromatic compound) rather that an unsaturated aliphatic alcohol. The case for aromaticity of vitamin C can be made using the four established criteria of aromaticity which includes planarity, conjugation, cyclic state and the Huckel rule set in 1931. The Huckel rule states that a cyclic, planar molecule is considered aromatic if it has $4n+2\pi$ electrons (the second bond of the double bond). The classic aromatic benzene has $6\pi$ electrons (3 double bonds, therefore n=1), is cyclic, planar and conjugated by resonance as shown in Figure. Vitamin C, on the other hand, has a 5-atom cyclic structure, is partially planar in 3 ring carbons, has two outside oxygens producing the required conjugation (see FIG. 5), and has $2\pi$ electrons, therefore n=0 by Huckel's rule definition. Accordingly, the aromaticity of vitamin C is fully supported by the four rules above and that conclusion facilitates the understanding of its antioxidant properties by grouping it with the phenolic antioxidants as an "aliphatic phenol." Further, as depicted in FIG. 6, vitamin C, as an antioxidant, can donate a hydrogen to the attacking hydroxyl radical producing water and an ascorbyl radical. The ascorbyl radical can then stabilize, like vitamin E, by hydroxyl radical addition to produce an unstable gem-diol that converts into dehydroascorbic acid, which undergoes dimerization and subsequent reactions.

Figure 7:
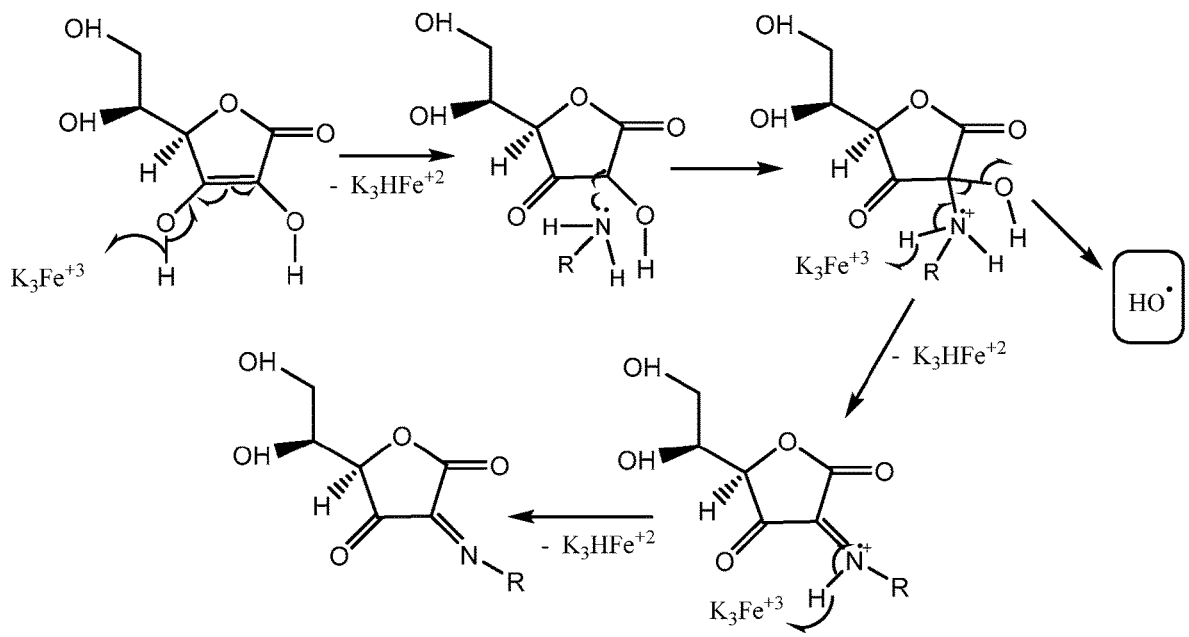
FIG. 7 illustrates a mechanism of reaction of vitamin C with potassium ferricyanide and an amino-containing compound (RNH2) to produce the general structure of the vitamin C imino-ketones.

According to an embodiment, potassium ferricyanide can act as a stable hydroxyl radical equivalent. As such, it can remove the hydrogen from the ascorbic acid forming the stable tri-potassium hydrogen ferrocyanide, but it cannot stabilize the ascorbyl radical any further as the hydroxyl radical does, so water or other co-adjuvants can serve as the providers of the electron for stabilization. Further, according to an embodiment, compounds that contain the amino group can serve as co-adjuvants in vivo when the level of hydroxyl radicals is low. The co-adjuvant behavior of amino-containing compounds is more pronounced when potassium ferricyanide is used as hydroxyl radical equivalent facilitating the formation of the compounds subject of the present disclosure, as shown mechanistically in FIG. 7. In general, such reactions require 3 units of ferricyanide per one unit of vitamin C and one unit of the amino-containing compound, represented by $RNH_2$ in FIG. 7. Also indicated in the figure, 3 units of the easily separable hydroxyl radical generator H-ferrocyanide ($K_3HFe^{+2}$ in the figure) can be made a useful by-product and also, prominently, a hydroxyl radical is released in the process.

According to an embodiment, the present invention provides for ketoimino compounds derived from vitamin C and the following formula:

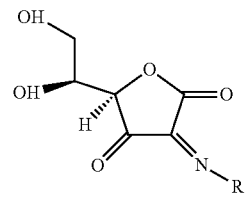

wherein R represents any amino-containing compound, natural or synthetic. According to an embodiment, the exemplary ketoimino compounds, due to their higher oxidation state and intrinsic resonance, can be highly stable and naturally endowed with a multiplicity of colors that resist changes in pH and temperature, with a solubility that can be easily modified with variations on the R substituent. According to an embodiment, when the substitutions are natural amino acids, the exemplary all-natural ketoimino compounds can mimic the colors of fruits and vegetables and, as such, can be safely used to naturally color drinks and cosmetics, and can also be used as a delivery form for vitamin C and the amino acids. In this regard, other useful compounds can be delivered through this system, including the natural vitamin B1 and amines used as drugs, such as the antidiabetic metformin. Further, the compounds described can be made through environmentally-friendly radical reactions that follow the antioxidant mechanism of action of vitamin C, described herein, in which water is used as the solvent and the byproducts are useful non-toxic materials.

Exemplary Method

According to an embodiment, a solution in water (or water/alcohol) of equimolar amounts of vitamin C (ascorbic acid) and the amino-containing compound can be added to a stirred solution of 3 equimolar amounts of potassium ferricyanide in water. The mixture can be stirred for 24 to 48 hours, and methanol can be added to precipitate the green potassium hydrogen ferrocyanide. Further, the solution can be concentrated, extracted with methanol, and filtered through a plug of silica gel to produce, after concentration, a colored solid of the ketoimino compound that can then be characterized by NMR and mass spectrometry.

Example 1

A 1:1 solution in water/ethanol (50 ml each) of 1.76 g of vitamin C (ascorbic acid) and 1.65 g of phenylalanine was added to a stirred solution of 9.9 g of potassium ferricyanide in 80 ml of water. The yellow color of the ferricyanide became green upon addition and completely dark green after 48 hours of stirring. Then, 300 ml of methanol were added and stirring continued for 1 hour, and the suspension produced was filtered. The filtrate was concentrated under vacuum to a solid that was dissolved in 100 ml of methanol and the solution was filtered through a plug of silica gel to remove remnants of the ferrocyanide by-product. The filtrate was concentrated under vacuum to produce 2.1 g (65% yield) of a dark red solid that solubilizes in water and in ethanol.

Example 2

A solution in water of 1.76 g of vitamin C (ascorbic acid) and 1.66 g of metformin hydrochloride was added to a stirred solution of 9.9 g of potassium ferricyanide in 80 ml of water. The yellow color of the ferricyanide became green upon addition and changed to blue green after 48 hours of stirring. Then, 300 ml of methanol were mixed and the suspension produced was filtered after stirring for 30 minutes. The filtrate was concentrated under vacuum to a solid that was dissolved in 100 ml of methanol and the solution was filtered through a plug of silica gel to remove remnants of the ferrocyanide by-product. The filtrate was concentrated under vacuum to produce 1.44 g (42% yield) of a yellow powdery solid that is freely soluble in water.

Example 3

A solution in water of 1.76 g of vitamin C (ascorbic acid) and 3.37 g of thiamine hydrochloride (vitamin B1) was added to a stirred solution of 9.9 g of potassium ferricyanide in 80 ml of water. The yellow color of the ferricyanide became apple green upon addition and changed to dark green after 48 hours of stirring. Then, 300 ml of methanol were mixed and the suspension produced was filtered after stirring for 30 minutes. The filtrate was concentrated under vacuum to a solid that was dissolved in 100 ml of methanol and the solution was filtered through a plug of silica gel to remove remnants of the ferrocyanide by-product. The filtrate was concentrated under vacuum to produce 1.50 g (33% yield) of a dark yellow solid that is freely soluble in water.

It is to be understood that the above described embodiments are merely illustrative of numerous and varied other embodiments which may constitute applications of the principles of the invention. Such other embodiments may be readily devised by those skilled in the art without departing from the spirit or scope of this invention and it is our intent they be deemed within the scope of our invention.

The foregoing detailed description of the present disclosure is to be understood as being in every respect illustrative and exemplary, but not restrictive, and the scope of the present disclosure provided herein is not to be determined solely from the detailed description, but rather from the claims as interpreted according to the full breadth and scope permitted by patent laws. It is to be understood that the embodiments shown and described herein are merely illustrative of the principles addressed by the present disclosure and that various modifications may be implemented by those skilled in the art without departing from the scope and spirit of the present disclosure. Those skilled in the art may implement various other feature combinations without departing from the scope and spirit of the present disclosure. The various functional modules shown are for illustrative purposes only, and may be combined, rearranged and/or otherwise modified.

The invention claimed is:

1. A compound of the following formula:

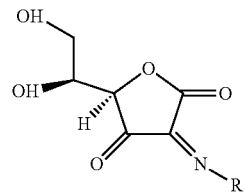

wherein R represents any amino-containing compound, wherein the amino-containing compound is attached through an imino bond.

2. The compound of claim 1, wherein the amino-containing compound is one of a natural or synthetic compound.

3. A method of synthesis of the compound in claim 1 by which the vitamin C reacts with potassium ferricyanide in a 1:3 chemical proportion producing a vitamin C radical that then adds to the amino-containing compound in a 1:1 chemical proportion.

4. A method of delivering the amino-containing compound in claim 1 through an attachment of the amino-containing compound to the vitamin C via an imino bond.

5. The method of claim 4, wherein the amino-containing compound is antidiabetic metformin.

6. The method of claim 4, wherein the amino-containing compound is vitamin B1.

7. The compound of claim 1, wherein the amino-containing compound is a mono amino acid.

* * * * *